US012644129B2

(12) United States Patent
Laan et al.

(10) Patent No.: US 12,644,129 B2
(45) Date of Patent: Jun. 2, 2026

(54) DOWNY MILDEW RESISTANT SPINACH PLANT

(71) Applicant: Bejo Zaden B.V., Warmenhuizen (NL)

(72) Inventors: Raimon Jozef Laan, Warmenhuizen (NL); Jordi Cornelis Boshoven, Warmenhuizen (NL); Stefanus Johannes Kaandorp, Warmenhuizen (NL); Roelof Marinus Veenstra, Warmenhuizen (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 0 days.

(21) Appl. No.: 18/956,775

(22) Filed: Nov. 22, 2024

(65) Prior Publication Data

US 2025/0084430 A1 Mar. 13, 2025

Related U.S. Application Data

(62) Division of application No. 17/614,158, filed as application No. PCT/EP2019/063959 on May 29, 2019, now Pat. No. 12,365,913.

(51) Int. Cl.
*C12N 15/82* (2006.01)
*C12Q 1/68* (2018.01)
*C12Q 1/6895* (2018.01)

(52) U.S. Cl.
CPC ....... *C12N 15/8282* (2013.01); *C12Q 1/6895* (2013.01); *C12Q 2600/13* (2013.01); *C12Q 2600/156* (2013.01)

(58) Field of Classification Search
CPC . C12Q 1/6895; C12Q 2600/156; A01H 6/028
See application file for complete search history.

(56) References Cited

U.S. PATENT DOCUMENTS

| | | | | |
|---|---|---|---|---|
| 10,813,319 | B2 * | 10/2020 | Koerber ................... | A01H 5/12 |
| 2017/0027126 | A1 | 2/2017 | Dijkstra et al. | |
| 2017/0055481 | A1 | 3/2017 | Brugmans et al. | |
| 2018/0206442 | A1 * | 7/2018 | Koerber ................. | A01H 6/028 |
| 2018/0206443 | A1 | 7/2018 | Koerber | |

FOREIGN PATENT DOCUMENTS

| | | |
|---|---|---|
| WO | 2015054339 A1 | 4/2015 |

OTHER PUBLICATIONS

Batley & Edwards, "SNP applications in plants," Association Mapping in Plants, Oraguzie et al., eds. Springer, Berlin, 95-102 (2007), p. 96. (Year: 2007).*
Ganal et al., Curr Opin Plant Biol 12:211-17 (2009), p. 211. (Year: 2009).*

Xu et al. (Published: 2016, Journal: Nature Communications, 8:15275, DOI: 10.1038/ncomms15275 |www.nature.com/naturecommunications) (Included with IDS submitted on Nov. 22, 2024). (Year: 2016).*
Monsanto Vegetable IP Management B.V., "*Spinacia oleracea* L.; SV1371VC; sv 1371VC", Community Plant Variety Office, Dec. 22, 2015, 11 pages.
Monsanto Vegetable IP Management B.V., "*Spinacia oleracea* L.; Bylot; svvc5613", Community Plant Variety Office, Feb. 14, 2019, 8 pages.
Xu et al., "Draft Genome of Spinach and Transcriptome Diversity of 120 Spinacia Accessions", Nature Communications, May 24, 2017, pp. 1-10.
Nunhems Netherlands B.V., Spinach Catalogue, pp. 1-7, publication 2021, Nunhems Netherlands B.V., www.nunhems.com.
Nunhems Netherlands B.V., US Variety Patents List, pp. 1-16, publication 2023, Nunhems Netherlands B.V., www.nunhems.com.
DNA Date Bank of Japan (DDBJ), Accession number data for 6 Accession numbers, pp. 1-6, publication 2023.
Fujito et al. "Evidence for a common origin of homomorphic and heteromorphic sex chromosomes in distinct Spinacia species." G3: Genes, Genomes, Genetics 5.8 (2015): 1663-1673. (Year 2015).
Definition of providing. https://merriam-webster.com/thesaurus/providing#:~: text=tp%20put%20(something)%20into%20the, furnishing; Accessed 01/34/2024. (Year: 2024).
Das et al., 2023, "Spinach (*Spinacia oleracea* L.) Breeding: From Classical to Genomics-Centric Approach. In Smart Plant Breeding for Vegetable Crops in Post-genomics Era" (pp. 117-142), Singapore: Springer Nature Singapore. (Year: 2023).
Xu et al., 2017, "Draft genome of spinach and transcriptome diversity of 120 Spinacia accessions." Nature Communications, 8(1), 15275. (Year: 2017).
Xu et al., 2017, "Draft genome of spinach and transcriptome diversity of 120 Spinacia accessions, Supplementary data." Nature Communications, 8(1), 15275. (Year: 2017).
Gyawali et al., 2021, "Genetic diversity, structure, and selective sweeps in Spinacia turkestanica associated with the domestication of cultivated spinach." Frontiers in Genetics, 12, 740437. (Year: 2021).

(Continued)

*Primary Examiner* — David H Kruse
*Assistant Examiner* — Santosh Sharma
(74) *Attorney, Agent, or Firm* — The Webb Law Firm

(57) ABSTRACT

The present invention relates to downy mildew, and especially downy mildew caused by the plant pathogen *Peronospora farinosa*, resistant spinach plants (*Spinacia oleracea*). The present spinach plants include a downy mildew resistance providing genomic fragment from *Spinacia tetrandra*. Specifically, the present invention relates to spinach plants being resistant to downy mildew, wherein the spinach plant includes a downy mildew resistance providing genomic fragment from *Spinacia tetrandra* such as spinach plants including in their genomes one or more nucleic acid sequences selected from the groups consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 and SEQ ID No. 35.

6 Claims, 3 Drawing Sheets

Specification includes a Sequence Listing.

(56) References Cited

OTHER PUBLICATIONS

Mauricio et al., "Mapping quantitative trail loci in plants: uses and caveats for evolutionary biology." Nature Review Genetics, 2(5), 370-381. (Year: 2001).

Li et al., 2023, "A rapid method for assembly of single chromosome and identification of sex determination region based on single-chromosome sequencing." New Phytologist, 240(2), 892-903. (Year: 2023).

Description of spinach variety Crater Loci LC763488 to LC763493, provided by Third PartyDNA Data Bank of Japan (DDBJ) https://ddbj.nig.ac.jp/index-e.html. Accessed Jan. 31, 2024.

* cited by examiner

DOWNY MILDEW RESISTANT SPINACH PLANT

CROSS-REFERENCE TO RELATED APPLICATIONS

This application is a divisional of U.S. patent application Ser. No. 17/614,158, filed May 29, 2019, which is the United States national phase of International Application No. PCT/EP2019/063959 filed May 29, 2019, the disclosures of which are hereby incorporated by reference in their entirety.

The Sequence Listing associated with this application is filed in electronic format via Patent Center and is hereby incorporated by reference into the specification in its entirety. The name of the file containing the Sequence Listing is 2107147.xml. The size of the file is 35,664 bytes, and the file was created on Nov. 15, 2024.

BACKGROUND OF THE INVENTION

Field of the Invention

The present invention relates to downy mildew, and especially downy mildew caused by the plant pathogen *Peronospora farinosa*, resistant spinach plants (*Spinacia oleracea*). The present spinach plants comprise a downy mildew resistance providing genomic fragment from *Spinacia tetrandra*. The present invention further relates to seeds and plant parts of the present plants, methods for providing, or identifying, the present plants and downy mildew resistance providing nucleic acid sequences.

Description of Related Art

Spinach is commercially grown worldwide for its attractive and nutritious leaves. In 2017, production of spinach was close to 28 million tons worldwide. Spinach (*Spinacia oleracea*) is a member of the Amaranthaceae family, subfamily Chenopodioideae. Other well-known family members include such plants as quinoa and beet. The latter is a cultivated plant of big importance for agriculture with sugar beet, red beet and Swiss chard as examples.

Regarding nutritional value, while providing only a small amount of calories (only 23 for 100 grams of cooked spinach), spinach is a rich source of vitamins A, B2 (or folate), B6, C, E and K; magnesium, manganese, calcium, potassium, iron and dietary fibre.

Spinach flowering is induced by (long) day length and under optimal conditions can reach even up to 4 generations in a year with a life cycle from seed to new harvest completed within 3 months. A bottleneck can be caused by seed dormancy.

Spinach is a wind pollinator and its pollen can reach far. A line is considered male if it converts from female or mixed flowering to (all) male flowering within a week. Female lines stay so for at least three weeks without producing any pollen. Hybrids of spinach can readily be produced making use of plants which have a female flowering phase and plants which have a male flowering phase as pollinator. Before the female plants develop male flowers, all female flowers are fertilized by the male plant. The setting of seeds occurs rapidly within 3 days and after that the ripening of the seed takes approximately a month.

Under optimal conditions commercial elite spinach lines are grown and harvested within 25 days to obtain baby leaf spinach.

Breeding resulted in spinach plants which are rapid growing without premature flowering. Older varieties tend to have narrower leaves and have a stronger, somewhat bitter taste; newer varieties have broader leaves and a milder taste. Also, recent types have little tendency for bolting in warm conditions and therefore will not prematurely flower and produce seeds.

Spinach is cultivated for the leaves. Commercial spinach can have round leaves of dark green color. The leaf morphology is of interest to spinach breeders. A significant share of the market of cultivated spinach is the early harvested baby leaf spinach. For spinach growers it is important that the leaves stand straight up which facilitates easy harvest, dark green colour is desired.

Spinach originates from middle Asia but it is now produced all over the world. Traditional areas where spinach was grown as a crop are Europe and Northern America, however contemporarily the biggest volume of spinach is produced in China. Spinach is produced for the food processing industry (canned or frozen spinach) as well as for the fresh market, where especially baby leaf spinach is in demand. Breeders develop lines with characteristics best suited for the location or the purpose.

An important development in the production and sales of fresh spinach was the introduction of bagged spinach. For this application the desired leaf morphology is such that the leaves are not too closely packed together that are found in the partly savoyed types.

Basic types of spinach are on the market:

A savoy type with dark green, curly and crinkly leaves (for the fresh market);

A flat, or smooth, leaf spinach with broad, smooth leaves that can be cleaned easily. This type is used for industry (canned or frozen spinach, as well as processed food and baby food;

Semi savoy is an intermediate type of spinach with a comparable texture as the savoy type but easy to clean as the smooth type of spinach. It is cultivated both for fresh market and industry.

An oriental type which is heat tolerant, has long petioles, pointed leaves with several side lobes and as plant has an upright growth.

Most spinach is produced at high plant density for fresh market production which creates the ideal environment for disease development. Additionally, there is an increasing demand to produce organic vegetables. Consumers are looking for vegetables that are obtained without the use of pesticides, fungicides, insecticides and without chemical treatment of the seed. The challenge here is that such production conditions often lead to the development of plant disease. This creates a need for spinach cultivars that encompass natural, genetically encoded resistance against pathogens.

The most common pathogens causing diseases of spinach are *Peronospora, Fusarium, Stemphyllium, Colletotrichum, Cercospora* and Cucumber Mosaic Virus. The most important disease in spinach is downy mildew caused by the oomycete pathogen *Peronospora effusa* (=*P. farinosa f.* sp. *spinaciae* [hereafter Pfs]). The short lifecycle of Pfs results in rapid multiplication of the pathogen on susceptible cultivars. At first, small pale yellow irregular spots appear on the upper surface of the leafs and a purple downy growth on the lower surface of the spots. Spores develop on the leaves 9-12 days after first infection and are spread by wind and splashes of water. Infected leafs are no longer attractive for consumption and prone to other, secondary (microbial) infections.

One way to combat downy mildew is to spray the plants with fungicide. This approach is highly undesirable due to its heavy impact on the environment and because it is cost and labour intense. Moreover, half of the agriculturally produced spinach is meant for the organic market and this approach is not suitable for this application. There is thus a strong need in the field for spinach with resistance against the pathogen.

*Peronospora farinosa* is a pathogen that rapidly overcomes resistance. Within 2 to 3 years newly introduced resistance genes can be broken by the pathogen and therefore there is a constant demand to identify new resistance sources. Seventeen official races have been described by the International Working group on *Peronospora effusa/farinosa*/Pfs (IWGP). Since only a limited set of Resistance to *Peronospora* (RPF) genes have been described that originate from *S. oleracea*, wild relatives are a potential interesting source of novel and alternative RPF genes.

*Spinacia tetrandra* and *Spinacia turkestanica* are wild relatives of the contemporary spinach. It is possible to cross *Spinacia oleracea* with these wild relatives and as such they can be important sources of genetically encoded resistance to plant pathogens. Morphologically they resemble ancient spinach *Spinacia oleracea*. They are also either male or female with pointy leaves with sharp angles.

Considering the above, there is a need in the art for novel resistance sources providing resistance to downy mildew.

SUMMARY OF THE INVENTION

It is an object of present invention to provide a solution for the above problems and needs of the art.

This object of the present invention, amongst other objects, is met as outlined in the appended claims.

Specifically, this object of the present invention, amongst other objects is met, according to a first aspect of the present invention by spinach plants being resistant to downy mildew, wherein the spinach plants comprise a downy mildew resistance providing genomic fragment from *Spinacia tetrandra*.

The present inventors have surprisingly discovered that a resistance in a wild relative of spinach could be successfully transferred to commercial spinach plants thereby providing downy mildew resistance to these plants.

According to a preferred embodiment, the present invention relates to spinach plants, wherein the genomic fragment from *Spinacia tetrandra* is located on chromosome 4 of the spinach plant.

According to another preferred embodiment, the present invention relates to a spinach plant, wherein the genomic fragment from *Spinacia tetrandra* is obtainable, or obtained, from a plant, representative seeds thereof have been deposited on 4 Apr. 2019 under deposit number NCIMB 43379 (National Collection of Industrial Food and Marine Bacteria, Ferguson Building, Craibstone Estate, Bucksburn, Aberdeen AB21 9YA, UK).

According to an especially preferred embodiment, the present spinach plants comprise in their genomes a genomic fragment from *Spinacia tetrandra*, the genomic fragment comprises one or more nucleic acid sequences selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 and SEQ ID No. 35.

According to another especially preferred embodiment, the present spinach plants do not comprise in their genomes a genomic fragment comprising one or more nucleic acid sequences selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22, SEQ ID No. 24, SEQ ID No. 26, SEQ ID No.28, SEQ ID No. 30, SEQ ID No. 32, SEQ ID No. 34 and SEQ ID No. 36.

The present spinach plants preferably are hybrids or inbred plants.

According to the present invention, the present spinach plants are preferably *Spinacia oleracea* plants.

According to a second aspect, the present invention relates to seeds, edible parts, pollen, egg cells, callus, suspension culture, somatic embryos, embryos or plant parts of the spinach plants defined above comprising a downy mildew resistance providing genomic fragment from *Spinacia tetrandra*.

According to a third aspect, the present invention relates to methods for identifying a spinach plant being resistant to downy mildew, the method comprises the step of establishing the presence of a genomic fragment comprising one or more nucleic acid sequences selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 and SEQ ID No. 35 in the genome of the spinach plant.

According to a fourth aspect, the present invention relates to the use of one or more genomic DNA sequences selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 and SEQ ID No. 35 for identifying or providing a spinach plant being resistant to downy mildew.

According to a fifth aspect, the present invention relates to methods for providing the present spinach plant being resistant to downy mildew, wherein the methods comprise introgressing a downy mildew resistance providing genomic fragment from *Spinacia tetrandra* into a spinach plant.

According to a sixth aspect, the present invention relates to nucleic acid sequences selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 and SEQ ID No. 35.

BRIEF DESCRIPTION OF THE DRAWINGS

The present invention is detailed in the following examples and figures wherein.

5

Figure 1:
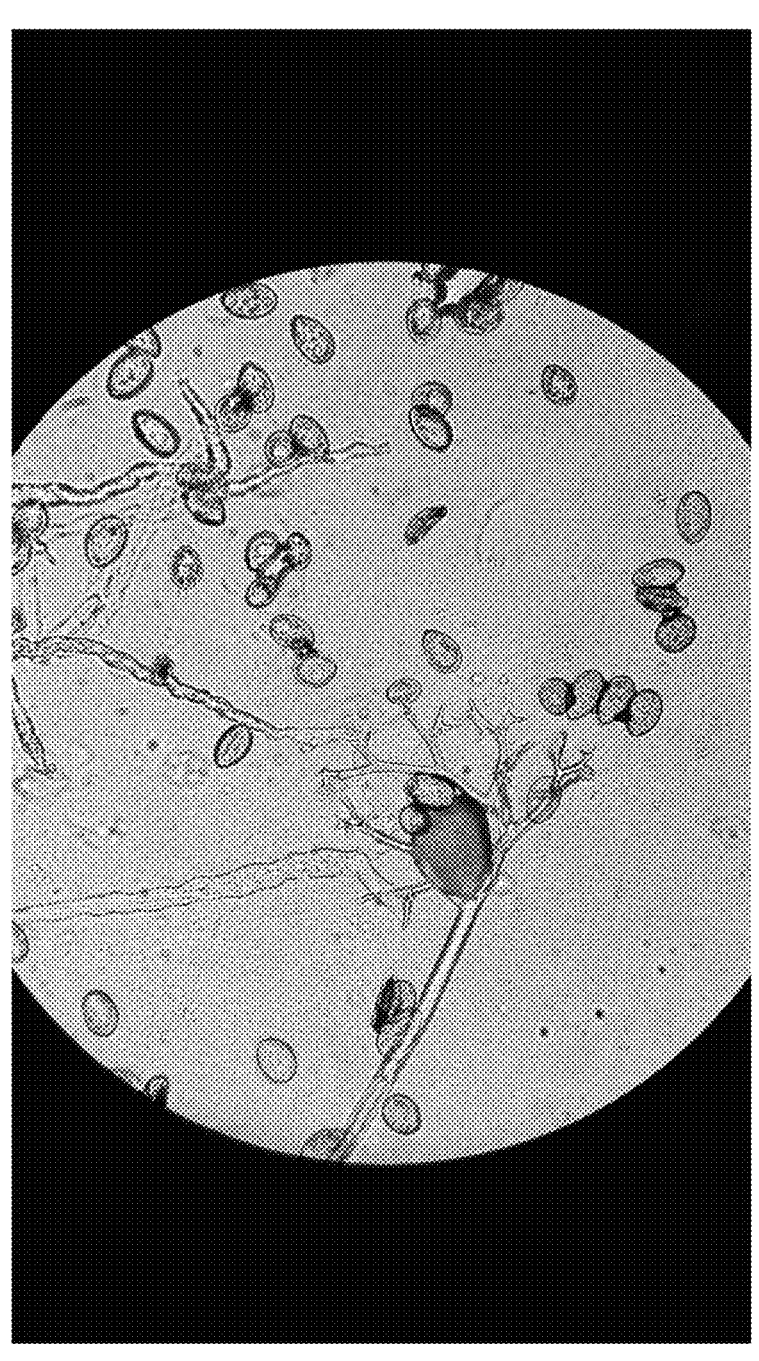
FIG. 1: shows a representative microscopy image of *P. farinosa f.* sp. *spinaciae;*
Figure 2:
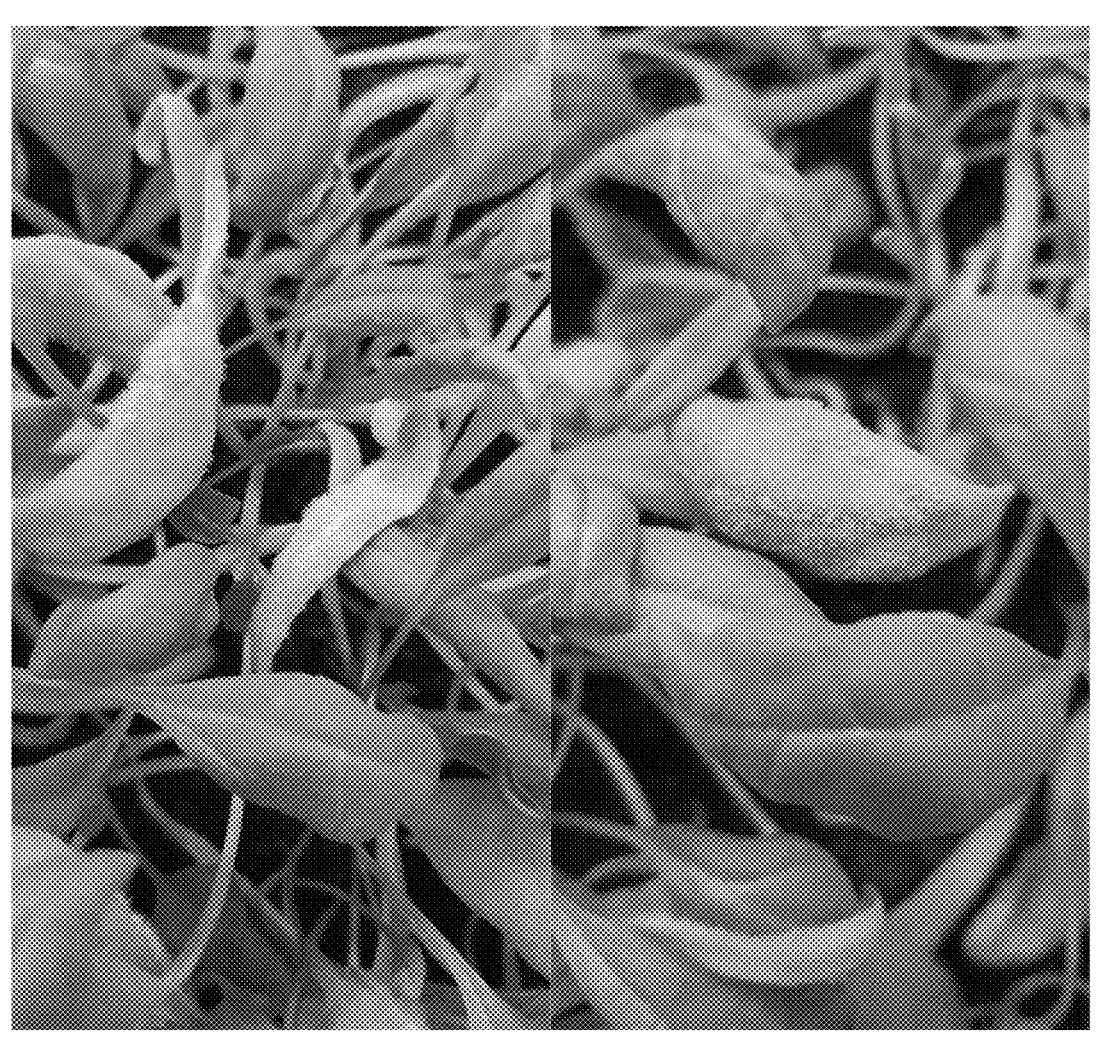
FIG. 2: shows a representative photograph of leaves of spinach plants infected with the downy mildew causative pathogen *Peronospora farinosa;*
Figure 3:

FIG. 3: shows a representative photograph of a spinach plant resistant to downy mildew.

DESCRIPTION OF THE INVENTION

Examples

Example 1. Breeding Scheme: Introducing *S. tetrandra* Resistance Against Downy Mildew Into *S. oleracea*

Initially, individual *Spinacia tetrandra* plants from CGN number CGN120251 were crossed with Blight A (*S. oleracea*). The latter is a female line which does not harbor any downy mildew resistance and therefore resistance in the offspring has to originate from the *Spinacia tetrandra* source. Blight A is an agriculturally elite line with round and dark leaves as its characteristics.

Result F1: Blight A×CGN120251.

Subsequently, downy mildew tests were performed with different races on the *S. tetrandra,-S. oleracea* hybrids. Per hybrid population, resistant and vital plants were put together in a pollen-tight bag with Blight A. The hybrid-plants were female and therefore it was necessary to wait for the pollen production of Blight A. In this generation Blight A was used as a father instead of being used as a mother. The seeds were harvested in bulk from the hybrid plants.

Result BC1: Blight A(2)×CGN120251

The seeds harvested from the hybrid were prickly. At first, the BC1 seeds did not germinate at all even when the embryos were grown in vitro. To overcome the dormancy the seeds were first incubated at 4° C. Hereafter, the pots were kept at 20° C. and the seeds were germinating. Subsequently, a Pfs race 11 downy mildew disease test was performed on the plants. The resistant plants were selected and individually crossed with Blight C (*S. oleracea*). Blight C is a male line that also lacks mildew resistance.

Result BC2: (Blight A(2)×CGN120251)×Blight C

To continue backcrossing, BC2 seed lots were selected on seed smoothness and yield. On the selected BC2 lots, another Pfs race 11 downy mildew test was performed. Resistant plants were selected and after that genotyped. Plants with highest resemblance to *Spinacia oleracea* (originating from Blight A or C) were selected. These plants were individually crossed with Blight A or C depending on the flowering behaviour of the BC2. In this example Blight C was used in this cross. Seeds were harvested from the backcross plant.

Result BC3: (Blight A(2)×CGN120251)×Blight C (2)

A Pfs strain 11 downy mildew test was performed on the BC3 plants. Resistant plants were genotyped to be able to select plants with the highest resemblance with *S. oleracea*. Selected plants were selfed.

Result BC3S1: ((Blight A(2)×CGN120251)×Blight C (2)) S1

Example 2. Description of Spinach Downy Mildew—*Peronospora farinosa*—Disease Trial Resistance to *Peronospora farinosa f.* sp. *spinaciae* (synonym *P. effusa* [hereafter Pfs]) is tested in a qualitative disease assay. In short, 10 to 14 days after untreated seed is sown in soil, a minimum of 8 plants is inoculated with a spore suspension of a single Pfs race or isolate. Pfs is maintained on a living susceptible host plant e.g. Viroflay or Blight or plant material with spores is stored for a maximum of 1 year at −20° C. Inoculated plants are incubated under plastic at high humidity (80-100%) and at a temperature ranging from 16° C.-20° C. After 24 hours plastic is removed, plants are assessed at 9 to 12 days after inoculation. When sporulation is observed on the cotyledons or true leaves a plant is considered susceptible and when no sporulation is observed a plant is considered resistant.

A differential set as described in Table 1 is included in each disease trial under the same environmental conditions to confirm the race. This differential set for Pfs was developed by the International Working Group on *Peronospora farinosa* (IWGP) and can be found on the website of the International Seed Federation (ISF). This differential set that consists of spinach varieties and near-isogenic lines (NILs) is used to determine the Pfs race. In this table "−" indicates resistance (no sporulation), "+" indicates susceptibility (sporulation), "(−)" indicates intermediate resistance (sparse sporulation on the tips of cotyledons), "n.t." indicates that the current strain was not tested. Seeds of this differential set and Pfs races can be obtained at Naktuinbouw (P.O. Box 40, NL-2370 AA, Roelofarendsveen, Netherlands, naktuinbouw.com).

TABLE 1

IWGP Spinach differential set for Pfs. Where "−" is resistant, "+" is susceptible and "(−)" indicates intermediate resistance.

| Variety/NIL | Race Pfs | | | | | | | | | | | | | | | | |
| --- | --- | --- | --- | --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 | 14 | 15 | 16 | 17 |
| Viroflay | + | + | + | + | + | + | + | + | + | + | + | + | + | + | + | + | + |
| NIL5 | − | − | + | + | + | + | + | + | + | + | + | + | + | + | + | + | + |
| NIL3 | − | + | − | + | − | + | + | − | − | + | − | − | + | − | + | − | + |
| NIL4 | − | − | − | − | + | + | + | + | + | + | + | + | + | + | − | + | + |
| NIL6 | − | + | − | − | − | + | − | + | + | + | − | + | (−) | + | − | − | + |
| NIL1 | − | − | − | − | − | − | − | + | − | + | − | + | − | + | − | − | + |
| NIL2 | − | − | − | − | − | − | − | − | − | − | + | + | + | + | − | + | + |
| Whale | − | − | − | (−) | − | (−) | (−) | − | − | (−) | − | − | + | − | (−) | − | + |
| Pigeon | − | − | − | − | − | − | − | − | − | − | − | − | − | + | − | + | + |
| Caladonia | − | − | − | − | − | − | − | − | − | − | − | − | − | − | + | − | + |
| Meerkat | − | − | − | − | − | − | − | − | − | − | − | − | − | − | − | + | (−) |
| Hydrus | − | − | − | − | − | − | − | − | − | − | − | − | − | − | − | − | − |

TABLE 2

Resistance pattern of deposit NCIMB 43379. Where "−"
is resistant and "+" is susceptible and "n.t." is not tested.

| | Race Pfs | | | | | | | | | | | | | | | | |
|---|---|---|---|---|---|---|---|---|---|---|---|---|---|---|---|---|---|
| Variety | 1 | 2 | 3 | 4 | 5 | 6 | 7 | 8 | 9 | 10 | 11 | 12 | 13 | 14 | 15 | 16 | 17 |
| Deposit 43379 | n.t. | n.t. | n.t. | − | n.t. | n.t. | − | n.t. | − | − | − | − | − | − | − | − | − |

Example 3. Novel Resistance Against Downy Mildew From *Spinacia tetrandra*—Marker Development In the BC2 population derived from *S. oleracea* and *S. tetrandra* crosses 56 Single Nucleotide Polymorphisms (SNPs) informative between both parents were used to genotype the population. The 56 SNPs were distributed across all six chromosomes. A correlation was found between the disease score and a SNP on chromosome 4 (Table 3). The correlation was not absolute, showing the identified SNP did not fully segregate with the resistance.

TABLE 3

Number of plants showing correlation between disease scores and the genotype of a SNP in a BC2 population derived from *S. oleracea* and *S. tetrandra*.

| Disease score Pfs11 | SNP* homozygous (*S. oleracea*) | SNP* heterozygous (*S. oleracea* and *S. tetrandra*) |
|---|---|---|
| Resistant | 6 | 16 |
| Susceptible | 20 | 2 |

*chromosome 4 position 11,627,232 bp.

The genomic region identified in the BC2 was genotyped for additional SNPs informative between both original parents. Resistant plants, heterozygous for the identified SNP, were selected and used to create BC3 populations. One BC3 population was challenged with several downy mildew isolates. A genomic region close to the SNP identified in the BC2 population segregated well with the disease scores (Table 4).

TABLE 4

Number of plants showing correlation between disease scores and the genotype of a genomic region in a BC3 population derived from *S. oleracea* and *S. tetrandra*.

| Downy mildew isolate | Resistant homozygous *S. oleracea** | Susceptible homozygous *S. oleracea** | Resistant heterozygous* | Susceptible Heterozygous* |
|---|---|---|---|---|
| Pf4 | 1 | 7 | 9 | 0 |
| Pf7 | 0 | 7 | 12 | 0 |
| Pf9 | 0 | 5 | 11 | 0 |
| Pf10 | 0 | 8 | 7 | 0 |
| Pf12 | 0 | 7 | 9 | 0 |
| Pf13 | 0 | 10 | 9 | 0 |
| Pf14 | 0 | 11 | 7 | 0 |
| Pf15 | 0 | 12 | 7 | 0 |
| Pf16 | 0 | 10 | 6 | 0 |
| Pf17 | 0 | 11 | 4 | 0 |
| Total | 1 | 88 | 81 | 0 |

*at identified genomic region.

The region co-segregating with the novel resistance from *S. tetrandra* is located on chromosome 4 between 8.0 and 8.9 Mbp and can be identified with several nucleotide sequences (Table 5). Abbreviations are according to IUPAC Nucleotide code.

TABLE 5

SNPsfor the detection of the resistance against *Peronospora farinosa*

| SNP | Chromosome | Position Chromosome* (bp) | Scaffold | Position Scaffold (bp) | Allele linked to resistance | Alternative allele |
|---|---|---|---|---|---|---|
| 1 | chr4 | 8,104,487 | 000037 | 700,416 | T | A |
| 2 | chr4 | 8,204,126 | 000037 | 800,055 | G | A |
| 3 | chr4 | 8,305,539 | 000037 | 901,468 | A | T |
| 4 | chr4 | 8,500,200 | 000037 | 1,096,129 | C | T |
| 5 | chr4 | 8,502,319 | 000037 | 1,098,248 | A | C |
| 6 | chr4 | 8,502,334 | 000037 | 1,098,263 | A | G |
| 7 | chr4 | 8,502,394 | 000037 | 1,098,323 | A | G |
| 8 | chr4 | 8,508,716 | 000037 | 1,104,645 | G | C |
| 9 | chr4 | 8,508,834 | 000037 | 1,104,763 | A | G |
| 10 | chr4 | 8,508,984 | 000037 | 1,104,913 | T | C |
| 11 | chr4 | 8,508,996 | 000037 | 1,104,925 | C | T |
| 12 | chr4 | 8,509,556 | 000037 | 1,105,485 | T | A |
| 13 | chr4 | 8,509,737 | 000037 | 1,105,666 | T | C |
| 14 | chr4 | 8,510,680 | 000037 | 1,106,609 | T | G |
| 15 | chr4 | 8,510,715 | 000037 | 1,106,644 | G | C |
| 16 | chr4 | 8,510,919 | 000037 | 1,106,848 | C | G |
| 17 | chr4 | 8,510,962 | 000037 | 1,106,891 | C | T |
| 18 | chr4 | 8,804,303 | 000037 | 1,400,232 | C | G |

*The reference genome is : Xu, C., et al., Draft genome of spinach and transcriptome diversity of 120 Spinacia accessions, Nature Communications 2017.

| SEQ ID No. | Genetic position* on Chr 4 (bp) | Sequence- SNP nucleotide is highlighted bold and in brackets |
|---|---|---|
| SEQ ID No. 1 | 8,104,487 | AGGGAATACTGGATTGTTGGAAGCGTATAAATTGTCAAGGMCCACAACAA[T] TATATGCCCACGAAAATAAACGCAAAAGTGATAACTGAATACTTTTCTAC |
| SEQ ID No. 2 | 8,104,487 | AGGGAATACTGGATTGTTGGAAGCGTATAAATTGTCAAGGMCCACAACAA[A] TATATGCCCACGAAAATAAACGCAAAAGTGATAACTGAATACTTTTCTAC |
| SEQ ID No. 3 | 8,204,126 | ATTCAAATCCAAATCAAATCCAGAAAAATTCAAAAAAAAAATACAAAATC[G] ACGCAGAAAACTTACAGAGAATGTCGCCGACGATTGACGCTGAAAATGCG |
| SEQ ID No. 4 | 8,204,126 | ATTCAAATCCAAATCAAATCCAGAAAAATTCAAAAAAAAAATACAAAATC[A] ACGCAGAAAACTTACAGAGAATGTCGCCGACGATTGACGCTGAAAATGCG |
| SEQ ID No. 5 | 8,305,539 | ATTTCTACCTTTTTTACGTACCACAATTCCACAAACTTGTGTATTTATAT[A] AACACTTTGGTCACACATTTCAACTACATTATTGCATTTCATTTCAATAY |
| SEQ ID No. 6 | 8,305,539 | ATTTCTACCTTTTTTACGTACCACAATTCCACAAACTTGTGTATTTATAT[T] AACACTTTGGTCACACATTTCAACTACATTATTGCATTTCATTTCAATAY |
| SEQ ID No. 7 | 8,500,200 | AGTTTTCTCACCTGAGCTCTGATGATAGCACTTTTCTTGTCTTGCTCAGC[C] TTTTCCACAATAAACTTGGCTCTTTCAGCATCTTGTGCAGCTACCTGTTT |
| SEQ ID No. 8 | 8,500,200 | AGTTTTCTCACCTGAGCTCTGATGATAGCACTTTTCTTGTCTTGCTCAGC[T] TTTTCCACAATAAACTTGGCTCTTTCAGCATCTTGTGCAGCTACCTGTTT |
| SEQ ID No. 9 | 8,502,319 | TCCTTGATACCAGAGATGCGGTTGAAGACGATAGCTCGATGACCACCTTC[A] ACATTGTACATACTRTGACTGACTCCATAAGCGGCAAGGCCAAGAGCACC |
| SEQ ID No. 10 | 8,502,319 | TCCTTGATACCAGAGATGCGGTTGAAGACGATAGCTCGATGACCACCTTC[C] ACATTGTACATACTRTGACTGACTCCATAAGCGGCAAGGCCAAGAGCACC |
| SEQ ID No. 11 | 8,502,334 | ATGCGGTTGAAGACGATAGCTCGATGACCACCTTCMACATTGTACATACT[A] TGACTGACTCCATAAGCGGCAAGGCCAAGAGCACCAAGAATTCCAACCTT |
| SEQ ID No. 12 | 8,502,334 | ATGCGGTTGAAGACGATAGCTCGATGACCACCTTCMACATTGTACATACT[G] TGACTGACTCCATAAGCGGCAAGGCCAAGAGCACCAAGAATTCCAACCTT |
| SEQ ID No. 13 | 8,502,394 | CCATAAGCGGCAAGGCCAAGAGCACCAAGAATTCCAACCTTAACCARATT[A] GCAGCAGCGCCACCGCCGCCACCAGGCATCTTGGGAACCTTAACGTTTTG |
| SEQ ID No. 14 | 8,502,394 | CCATAAGCGGCAAGGCCAAGAGCACCAAGAATTCCAACCTTAACCARATT[G] GCAGCAGCGCCACCGCCGCCACCAGGCATCTTGGGAACCTTAACGTTTTG |
| SEQ ID No. 15 | 8,508,716 | AGATTTCTGATTTCCTGTAGTTGGGAGTTTGATTCTTCCAGTTTCGGACA[G] AGAGGAAAATTTCTCAAATTATCACAAAATGTAATTAACAGATGAGAAAG |
| SEQ ID No. 16 | 8,508,716 | AGATTTCTGATTTCCTGTAGTTGGGAGTTTGATTCTTCCAGTTTCGGACA[C] AGAGGAAAATTTCTCAAATTATCACAAAATGTAATTAACAGATGAGAAAG |
| SEQ ID No. 17 | 8,508,834 | AATGTGWTTGAAACCCTGCTACTTCTCGTGTCTCACCCATATCTGATTCT[A] ATTTCCACCATCCTTCCAACTTTGGCATACTCCAAAGCTCAAGCTTTTCA |
| SEQ ID No. 18 | 8,508,834 | AATGTGWTTGAAACCCTGCTACTTCTCGTGTCTCACCCATATCTGATTCT[G] ATTTCCACCATCCTTCCAACTTTGGCATACTCCAAAGCTCAAGCTTTTCA |
| SEQ ID No. 19 | 8,508,984 | CTCCTGATGTTGATGCAACCCCTTCTGCGCTGATAGTACTATTCTCCATA[T] ACACCACTTCAYTCAAATATCGTAATGTAAGGAATTTCAAATGACGCAGT |
| SEQ ID No. 20 | 8,508,984 | CTCCTGATGTTGATGCAACCCCTTCTGCGCTGATAGTACTATTCTCCATA[C] ACACCACTTCAYTCAAATATCGTAATGTAAGGAATTTCAAATGACGCAGT |
| SEQ ID No. 21 | 8,508,996 | ATGCAACCCCTTCTGCGCTGATAGTACTATTCTCCATAYACACCACTTCA[C] TCAAATATCGTAATGTAAGGAATTTCAAATGACGCAGTTGACTCATCAAT |
| SEQ ID No. 22 | 8,508,996 | ATGCAACCCCTTCTGCGCTGATAGTACTATTCTCCATAYACACCACTTCA[T] TCAAATATCGTAATGTAAGGAATTTCAAATGACGCAGTTGACTCATCAAT |
| SEQ ID No. 23 | 8,509,556 | GGCATATGYGACAAACTCTTACAGCCTTGTATATCTAGGTGCCTTAGATT[T] ACTAATTTCCTCAAATCGCTTGGCAAAGTTTTTAGACCACGACACTCACG |
| SEQ ID No. 24 | 8,509,556 | GGCATATGYGACAAACTCTTACAGCCTTGTATATCTAGGTGCCTTAGATT[A] ACTAATTTCCTCAAATCGCTTGGCAAAGTTTTTAGACCACGACACTCACG |
| SEQ ID No. 25 | 8,509,737 | GATATCTTAGATGCAACAAGTTACCTATCTCACTCGGCAACATTTCCAAA[T] CAGAGTTATTCAAGCTTAAGACCCTTAAATATTCCACTTTTGATAACAAA |

-continued

| SEQ ID No. | Genetic position* on Chr 4 (bp) | Sequence-SNP nucleotide is highlighted bold and in brackets |
|---|---|---|
| SEQ ID No. 26 | 8,509,737 | GATATCTTAGATGCAACAAGTTACCTATCTCACTCGGCAACATTTCCAAA[C]<br>CAGAGTTATTCAAGCTTAAGACCCTTAAATATTCCACTTTTGATAACAAA |
| SEQ ID No. 27 | 8,510,680 | TACATCATCCAAAACAAGGAGGTATATCTTCCCATCCAGTTCGTCCCGAA[T]<br>TTTCATCTGAAGCTGGTCCATACTCATACTCAGGSCATCGTGCTTTCTTC |
| SEQ ID No. 28 | 8,510,680 | TACATCATCCAAAACAAGGAGGTATATCTTCCCATCCAGTTCGTCCCGAA[G]<br>TTTCATCTGAAGCTGGTCCATACTCATACTCAGGSCATCGTGCTTTCTTC |
| SEQ ID No. 29 | 8,510,715 | CCAGTTCGTCCCGAAKTTTCATCTGAAGCTGGTCCATACTCATACTCAGG[G]<br>CATCGTGCTTTCTTCTAGGGTTTACGGCTGCAAGGATTTCAGCAACAAGA |
| SEQ ID No. 30 | 8,510,715 | CCAGTTCGTCCCGAAKTTTCATCTGAAGCTGGTCCATACTCATACTCAGG[C]<br>CATCGTGCTTTCTTCTAGGGTTTACGGCTGCAAGGATTTCAGCAACAAGA |
| SEQ ID No. 31 | 8,510,919 | CCAGCCCCCCAATCCCCACTATGCTGACAACAGAAATATCCTTCTCCTCA[C]<br>AAGAAGTGTTTAGTACCATATCTATCACTTTCCGCTTGTCATYATCCCTC |
| SEQ ID No. 32 | 8,510,919 | CCAGCCCCCCAATCCCCACTATGCTGACAACAGAAATATCCTTCTCCTCA[G]<br>AAGAAGTGTTTAGTACCATATCTATCACTTTCCGCTTGTCATYATCCCTC |
| SEQ ID No. 33 | 8,510,962 | CTCCTCASAAGAAGTGTTTAGTACCATATCTATCACTTTCCGCTTGTCAT[C]<br>ATCCCTCCCAATGATCATATCTTCCTCGCAAACAAAGGAATGAGTTTCCC |
| SEQ ID No. 34 | 8,510,962 | CTCCTCASAAGAAGTGTTTAGTACCATATCTATCACTTTCCGCTTGTCAT[T]<br>ATCCCTCCCAATGATCATATCTTCCTCGCAAACAAAGGAATGAGTTTCCC |
| SEQ ID No. 35 | 8,804,303 | TAATTGATGATTTGAAGATTTATTACTACAACRCAATGGATTTTGTTTTG[C]<br>AATTATGCATTAAGAAGAGACTCRCATTTTTCATATTGGTGTATGGTAGT |
| SEQ ID No. 36 | 8,804,303 | TAATTGATGATTTGAAGATTTATTACTACAACRCAATGGATTTTGTTTTG[G]<br>AATTATGCATTAAGAAGAGACTCRCATTTTTCATATTGGTGTATGGTAGT |

*The reference genome is Xu, C., et al., Draft genome of spinach and transcriptome diversity of 120 Spinacia accessions, Nature Communications 2017.
Odd sequences = linked to resistance,
Even sequences = alternative allele.

What is claimed is:

1. A hybrid *Spinacia oleracea* plant being resistant to downy mildew and comprising in its genome, on chromosome 4 thereof, a nucleic acid fragment from *S. tetrandra* comprising a downy mildew resistance locus comprising SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, and SEQ ID NO: 33, wherein representative seeds possessing said nucleic acid fragment are deposited with NCIMB under Accession No. 43379.

2. The spinach plant according to claim 1, wherein the nucleic acid fragment from *Spinacia tetrandra* is from a plant, representative seeds thereof have been deposited under deposit number NCIMB 43379.

3. The spinach plant according to claim 1, wherein the nucleic acid fragment further comprises one or more nucleic acid sequences selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, and SEQ ID NO: 35.

4. The spinach plant according to claim 1, wherein the spinach plant does not comprise in its genome a genomic fragment comprising one or more nucleic acid sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO:28, SEQ ID NO: 30, SEQ ID NO: 32, SEQ ID NO: 34 and SEQ ID NO: 36.

5. A seed, edible parts, pollen, egg cells, callus, suspension culture, somatic embryos, embryos, or plant parts of a spinach plant according to claim 1, comprising the nucleic acid fragment from *Spinacia tetrandra*.

6. A method for providing spinach plant being resistant to downy mildew comprising introgressing a nucleic acid fragment from chromosome 4 of *Spinacia tetrandra* into a *S. oleracea* plant, the nucleic acid fragment comprising a downy mildew resistance locus comprising SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, and SEQ ID NO: 33, wherein representative seeds possessing said nucleic acid fragment are deposited with NCIMB under Accession No. 43379.

\* \* \* \* \*

SEQUENCE LISTING

Sequence total quantity: 36
SEQ ID NO: 1          moltype = DNA  length = 101
FEATURE               Location/Qualifiers
source                1..101
                      mol_type = genomic DNA
                      organism = Spinacia tetrandra
SEQUENCE: 1
aggggaatact ggattgttgg aagcgtataa attgtcaagg mccacaacaa ttatatgccc  60
acgaaaataa acgcaaaagt gataactgaa tacttttcta c                      101

SEQ ID NO: 2          moltype = DNA  length = 101
FEATURE               Location/Qualifiers
source                1..101
                      mol_type = genomic DNA
                      organism = Spinacia oleracea
SEQUENCE: 2
aggggaatact ggattgttgg aagcgtataa attgtcaagg mccacaacaa atatatgccc  60
acgaaaataa acgcaaaagt gataactgaa tacttttcta c                      101

SEQ ID NO: 3          moltype = DNA  length = 101
FEATURE               Location/Qualifiers
source                1..101
                      mol_type = genomic DNA
                      organism = Spinacia tetrandra
SEQUENCE: 3
attcaaatcc aaatcaaatc cagaaaaatt caaaaaaaaa atacaaaatc gacgcagaaa  60
acttacagag aatgtcgccg acgattgacg ctgaaaatgc g                      101

SEQ ID NO: 4          moltype = DNA  length = 101
FEATURE               Location/Qualifiers
source                1..101

-continued

```
                         mol_type = genomic DNA
                         organism = Spinacia oleracea
SEQUENCE: 4
attcaaatcc aaatcaaatc cagaaaaatt caaaaaaaaa atacaaaatc aacgcagaaa   60
acttacagag aatgtcgccg acgattgacg ctgaaaatgc g                        101

SEQ ID NO: 5              moltype = DNA   length = 101
FEATURE                  Location/Qualifiers
source                   1..101
                         mol_type = genomic DNA
                         organism = Spinacia tetrandra
SEQUENCE: 5
atttctacct tttttacgta ccacaattcc acaaacttgt gtatttatat aaacactttg   60
gtcacacatt tcaactacat tattgcattt catttcaata y                        101

SEQ ID NO: 6              moltype = DNA   length = 101
FEATURE                  Location/Qualifiers
source                   1..101
                         mol_type = genomic DNA
                         organism = Spinacia oleracea
SEQUENCE: 6
atttctacct tttttacgta ccacaattcc acaaacttgt gtatttatat aaacactttg   60
gtcacacatt tcaactacat tattgcattt catttcaata y                        101

SEQ ID NO: 7              moltype = DNA   length = 101
FEATURE                  Location/Qualifiers
source                   1..101
                         mol_type = genomic DNA
                         organism = Spinacia tetrandra
SEQUENCE: 7
agttttctca cctgagctct gatgatagca cttttcttgt cttgctcagc cttttccaca   60
ataaacttgg ctctttcagc atcttgtgca gctacctgtt t                        101

SEQ ID NO: 8              moltype = DNA   length = 101
FEATURE                  Location/Qualifiers
source                   1..101
                         mol_type = genomic DNA
                         organism = Spinacia oleracea
SEQUENCE: 8
agttttctca cctgagctct gatgatagca cttttcttgt cttgctcagc tttttccaca   60
ataaacttgg ctctttcagc atcttgtgca gctacctgtt t                        101

SEQ ID NO: 9              moltype = DNA   length = 101
FEATURE                  Location/Qualifiers
source                   1..101
                         mol_type = genomic DNA
                         organism = Spinacia tetrandra
SEQUENCE: 9
tccttgatac cagagatgcg gttgaagacg atagctcgat gaccaccttc aacattgtac   60
atactrtgac tgactccata agcggcaagg ccaagagcac c                        101

SEQ ID NO: 10             moltype = DNA   length = 101
FEATURE                  Location/Qualifiers
source                   1..101
                         mol_type = genomic DNA
                         organism = Spinacia oleracea
SEQUENCE: 10
tccttgatac cagagatgcg gttgaagacg atagctcgat gaccaccttc cacattgtac   60
atactrtgac tgactccata agcggcaagg ccaagagcac c                        101

SEQ ID NO: 11             moltype = DNA   length = 101
FEATURE                  Location/Qualifiers
source                   1..101
                         mol_type = genomic DNA
                         organism = Spinacia tetrandra
SEQUENCE: 11
atgcggttga agacgatagc tcgatgacca ccttcmacat tgtacatact atgactgact   60
ccataagcgg caaggccaag agcaccaaga attccaacct t                        101

SEQ ID NO: 12             moltype = DNA   length = 101
FEATURE                  Location/Qualifiers
source                   1..101
                         mol_type = genomic DNA
                         organism = Spinacia oleracea
SEQUENCE: 12
atgcggttga agacgatagc tcgatgacca ccttcmacat tgtacatact gtgactgact   60
ccataagcgg caaggccaag agcaccaaga attccaacct t                        101

SEQ ID NO: 13             moltype = DNA   length = 101
```

-continued

```
FEATURE                 Location/Qualifiers
source                  1..101
                        mol_type = genomic DNA
                        organism = Spinacia tetrandra
SEQUENCE: 13
ccataagcgg caaggccaag agcaccaaga attccaacct taaccaratt agcagcagcg   60
ccaccgccgc caccaggcat cttgggaacc ttaacgtttt g                      101

SEQ ID NO: 14         moltype = DNA   length = 101
FEATURE                 Location/Qualifiers
source                  1..101
                        mol_type = genomic DNA
                        organism = Spinacia oleracea
SEQUENCE: 14
ccataagcgg caaggccaag agcaccaaga attccaacct taaccaratt ggcagcagcg   60
ccaccgccgc caccaggcat cttgggaacc ttaacgtttt g                      101

SEQ ID NO: 15         moltype = DNA   length = 101
FEATURE                 Location/Qualifiers
source                  1..101
                        mol_type = genomic DNA
                        organism = Spinacia tetrandra
SEQUENCE: 15
agatttctga tttcctgtag ttgggagttt gattcttcca gtttcggaca gagaggaaaa   60
tttctcaaat tatcacaaaa tgtaattaac agatgagaaa g                      101

SEQ ID NO: 16         moltype = DNA   length = 101
FEATURE                 Location/Qualifiers
source                  1..101
                        mol_type = genomic DNA
                        organism = Spinacia oleracea
SEQUENCE: 16
agatttctga tttcctgtag ttgggagttt gattcttcca gtttcggaca cagaggaaaa   60
tttctcaaat tatcacaaaa tgtaattaac agatgagaaa g                      101

SEQ ID NO: 17         moltype = DNA   length = 101
FEATURE                 Location/Qualifiers
source                  1..101
                        mol_type = genomic DNA
                        organism = Spinacia tetrandra
SEQUENCE: 17
aatgtgwttg aaaccctgct acttctcgtg tctcacccat atctgattct aatttccacc   60
atccttccaa ctttggcata ctccaaagct caagcttttc a                      101

SEQ ID NO: 18         moltype = DNA   length = 101
FEATURE                 Location/Qualifiers
source                  1..101
                        mol_type = genomic DNA
                        organism = Spinacia oleracea
SEQUENCE: 18
aatgtgwttg aaaccctgct acttctcgtg tctcacccat atctgattct gatttccacc   60
atccttccaa ctttggcata ctccaaagct caagcttttc a                      101

SEQ ID NO: 19         moltype = DNA   length = 101
FEATURE                 Location/Qualifiers
source                  1..101
                        mol_type = genomic DNA
                        organism = Spinacia tetrandra
SEQUENCE: 19
ctcctgatgt tgatgcaacc ccttctgcgc tgatagtact attctccata tacaccactt   60
caytcaaata tcgtaatgta aggaatttca aatgacgcag t                      101

SEQ ID NO: 20         moltype = DNA   length = 101
FEATURE                 Location/Qualifiers
source                  1..101
                        mol_type = genomic DNA
                        organism = Spinacia oleracea
SEQUENCE: 20
ctcctgatgt tgatgcaacc ccttctgcgc tgatagtact attctccata cacaccactt   60
caytcaaata tcgtaatgta aggaatttca aatgacgcag t                      101

SEQ ID NO: 21         moltype = DNA   length = 101
FEATURE                 Location/Qualifiers
source                  1..101
                        mol_type = genomic DNA
                        organism = Spinacia tetrandra
SEQUENCE: 21
atgcaacccc ttctgcgctg atagtactat tctccataya caccacttca ctcaaatatc   60
gtaatgtaag gaatttcaaa tgacgcagtt gactcatcaa t                      101
```

-continued

```
SEQ ID NO: 22              moltype = DNA   length = 101
FEATURE                    Location/Qualifiers
source                     1..101
                           mol_type = genomic DNA
                           organism = Spinacia oleracea
SEQUENCE: 22
atgcaacccc ttctgcgctg atagtactat tctccataya caccacttca ttcaaatatc   60
gtaatgtaag gaatttcaaa tgacgcagtt gactcatcaa t                       101

SEQ ID NO: 23              moltype = DNA   length = 101
FEATURE                    Location/Qualifiers
source                     1..101
                           mol_type = genomic DNA
                           organism = Spinacia tetrandra
SEQUENCE: 23
ggcatatgyg acaaactctt acagccttgt atatctaggt gccttagatt tactaatttc   60
ctcaaatcgc ttggcaaagt ttttagacca cgacactcac g                       101

SEQ ID NO: 24              moltype = DNA   length = 100
FEATURE                    Location/Qualifiers
source                     1..100
                           mol_type = genomic DNA
                           organism = Spinacia oleracea
SEQUENCE: 24
gcatatgyga caaactctta cagccttgta tatctaggtg ccttagatta actaatttcc   60
tcaaatcgct tggcaaagtt tttagaccac gacactcacg                         100

SEQ ID NO: 25              moltype = DNA   length = 101
FEATURE                    Location/Qualifiers
source                     1..101
                           mol_type = genomic DNA
                           organism = Spinacia tetrandra
SEQUENCE: 25
gatatcttag atgcaacaag ttacctatct cactcggcaa catttccaaa tcagagttat   60
tcaagcttaa gacccttaaa tattccactt ttgataacaa a                       101

SEQ ID NO: 26              moltype = DNA   length = 101
FEATURE                    Location/Qualifiers
source                     1..101
                           mol_type = genomic DNA
                           organism = Spinacia oleracea
SEQUENCE: 26
gatatcttag atgcaacaag ttacctatct cactcggcaa catttccaaa ccagagttat   60
tcaagcttaa gacccttaaa tattccactt ttgataacaa a                       101

SEQ ID NO: 27              moltype = DNA   length = 101
FEATURE                    Location/Qualifiers
source                     1..101
                           mol_type = genomic DNA
                           organism = Spinacia tetrandra
SEQUENCE: 27
tacatcatcc aaaacaagga ggtatatctt cccatccagt tcgtcccgaa ttttcatctg   60
aagctggtcc atactcatac tcaggscatc gtgctttctt c                       101

SEQ ID NO: 28              moltype = DNA   length = 101
FEATURE                    Location/Qualifiers
source                     1..101
                           mol_type = genomic DNA
                           organism = Spinacia oleracea
SEQUENCE: 28
tacatcatcc aaaacaagga ggtatatctt cccatccagt tcgtcccgaa gtttcatctg   60
aagctggtcc atactcatac tcaggscatc gtgctttctt c                       101

SEQ ID NO: 29              moltype = DNA   length = 101
FEATURE                    Location/Qualifiers
source                     1..101
                           mol_type = genomic DNA
                           organism = Spinacia tetrandra
SEQUENCE: 29
ccagttcgtc ccgaaktttc atctgaagct ggtccatact catactcagg gcatcgtgct   60
ttcttctagg gtttacggct gcaaggattt cagcaacaag a                       101

SEQ ID NO: 30              moltype = DNA   length = 101
FEATURE                    Location/Qualifiers
source                     1..101
                           mol_type = genomic DNA
                           organism = Spinacia oleracea
SEQUENCE: 30
```

-continued

```
ccagttcgtc ccgaaktttc atctgaagct ggtccatact catactcagg ccatcgtgct   60
ttcttctagg gtttacggct gcaaggattt cagcaacaag a                        101

SEQ ID NO: 31          moltype = DNA   length = 101
FEATURE                Location/Qualifiers
source                 1..101
                       mol_type = genomic DNA
                       organism = Spinacia tetrandra
SEQUENCE: 31
ccagcccccc aatccccact atgctgacaa cagaaatatc cttctcctca caagaagtgt   60
ttagtaccat atctatcact ttccgcttgt catyatccct c                        101

SEQ ID NO: 32          moltype = DNA   length = 101
FEATURE                Location/Qualifiers
source                 1..101
                       mol_type = genomic DNA
                       organism = Spinacia oleracea
SEQUENCE: 32
ccagcccccc aatccccact atgctgacaa cagaaatatc cttctcctca gaagaagtgt   60
ttagtaccat atctatcact ttccgcttgt catyatccct c                        101

SEQ ID NO: 33          moltype = DNA   length = 101
FEATURE                Location/Qualifiers
source                 1..101
                       mol_type = genomic DNA
                       organism = Spinacia tetrandra
SEQUENCE: 33
ctcctcasaa gaagtgttta gtaccatatc tatcactttc cgcttgtcat catccctccc   60
aatgatcata tcttcctcgc aaacaaagga atgagtttcc c                        101

SEQ ID NO: 34          moltype = DNA   length = 101
FEATURE                Location/Qualifiers
source                 1..101
                       mol_type = genomic DNA
                       organism = Spinacia oleracea
SEQUENCE: 34
ctcctcasaa gaagtgttta gtaccatatc tatcactttc cgcttgtcat tatccctccc   60
aatgatcata tcttcctcgc aaacaaagga atgagtttcc c                        101

SEQ ID NO: 35          moltype = DNA   length = 101
FEATURE                Location/Qualifiers
source                 1..101
                       mol_type = genomic DNA
                       organism = Spinacia tetrandra
SEQUENCE: 35
taattgatga tttgaagatt tattactaca acrcaatgga ttttgttttg caattatgca   60
ttaagaagag actcrcattt ttcatattgg tgtatggtag t                        101

SEQ ID NO: 36          moltype = DNA   length = 101
FEATURE                Location/Qualifiers
source                 1..101
                       mol_type = genomic DNA
                       organism = Spinacia oleracea
SEQUENCE: 36
taattgatga tttgaagatt tattactaca acrcaatgga ttttgttttg gaattatgca   60
ttaagaagag actcrcattt ttcatattgg tgtatggtag t                        101
```